United States Patent [19]

Shiozaki et al.

[11] Patent Number: 5,973,198
[45] Date of Patent: Oct. 26, 1999

[54] METHOD FOR SEPARATING AMMONIUM SULFATE AND AMMONIUM BISULFATE FROM EACH OTHER AND PROCESS FOR PRODUCING 2-HYDROXY-4-METHYLTHIOBUTANOIC ACID UTILIZING THE METHOD

[75] Inventors: Tetsuya Shiozaki, Saijo; Kenji Ikudome, Niihama, both of Japan

[73] Assignee: Sumitomo Chemical Company, Limited, Osaka, Japan

[21] Appl. No.: 09/032,953

[22] Filed: Mar. 2, 1998

[30] Foreign Application Priority Data

Mar. 4, 1997 [JP] Japan .................................... 9-049029
Sep. 12, 1997 [JP] Japan .................................... 9-248592

[51] Int. Cl.$^6$ ........................... C07C 51/16; C07C 315/00
[52] U.S. Cl. ........................................... 562/526; 562/581
[58] Field of Search ..................................... 502/526, 581

[56] References Cited

U.S. PATENT DOCUMENTS

| | | |
|---|---|---|
| 3,709,666 | 1/1973 | Van Westerveld . |
| 3,902,859 | 9/1975 | Greco . |
| 4,524,077 | 6/1985 | Ruest et al. . |
| 4,912,257 | 3/1990 | Hernandez et al. . |
| 5,498,790 | 3/1996 | Grendel et al. . |

FOREIGN PATENT DOCUMENTS

| | | |
|---|---|---|
| 0126058 | 11/1984 | European Pat. Off. . |
| 0142488 | 5/1985 | European Pat. Off. . |
| 0330527 | 8/1989 | European Pat. Off. . |
| 2406623 | 5/1979 | France . |
| 2006778 | 5/1979 | United Kingdom . |
| 9428717 | 12/1994 | WIPO . |
| 9640630 | 12/1996 | WIPO . |

OTHER PUBLICATIONS

Database WPI, Section Ch, Week 7720, Derwent Publications, Class C04, An 77–35465Y Oct. 6, 1975.
Patent Abstract of Japan, Publication No. 08157447, Matsuoka Kazuyuki, Production of 2–Hydroxymethylmercaptobutyric Acid Jun. 18, 1996.

*Primary Examiner*—Paul J. Killos
*Attorney, Agent, or Firm*—Stevens, Davis, Miller & Mosher, L.L.P.

[57] ABSTRACT

A process for producing 2-hydroxy-4-methylthiobutanoic acid which includes conducting hydration and successive hydrolysis of 2-hydroxy-4-methylthiobutyronitrile in a reaction system containing 2-hydroxy-4-methylthiobutyronitrile and sulfuric acid, ammonium bisulfate being added to the reaction system at the time of the hydration and/or the hydrolysis, acquiring 2-hydroxy-4-methylthiobutanoic acid from the resulting organic layer, adding a water-miscible organic solvent to the by-produced aqueous layer to deposit ammonium sulfate, and separating and removing the ammonium sulfate from ammonium bisulfate, thereby permitting recycling and reusing of ammonium bisulfate, reduces the amount of sulfuric acid used, produces substantially no waste water containing sulfates and is of a low production cost and environmentally friendly.

5 Claims, 2 Drawing Sheets

METHOD FOR SEPARATING AMMONIUM SULFATE AND AMMONIUM BISULFATE FROM EACH OTHER AND PROCESS FOR PRODUCING 2-HYDROXY-4-METHYLTHIOBUTANOIC ACID UTILIZING THE METHOD

FIELD OF THE INVENTION

The present invention relates to a process for producing 2-hydroxy-4-methylthiobutanoic acid useful as a feed additive and the like. In more particular, it relates to a method for separating ammonium sulfate and ammonium bisulfate from each other and a process for producing 2-hydroxy-4-methylthiobutanoic acid utilizing the method.

BACKGROUND OF THE INVENTION

Heretofore, 2-hydroxy-4-methylthiobutanoic acid has been produced by a process which comprises reacting 2-hydroxy-4-methylthiobutyronitrile with an equal molar or slight excess of sulfuric acid to hydrate and hydrolyze the nitrile compound, and separating the resulting reaction liquid into an aqueous layer and an oil layer containing 2-hydroxy-4-methylthiobutanoic acid. The aqueous layer, which contains ammonium bisulfate, is discarded without any after-treatment or discarded after neutralized with ammonia to form ammonium sulfate which is deposited and separated therefrom, see for example, U.S. Pat. No. 4,524,077 and U.S. Pat. No. 4,912,257. This process, however, is not an industrially recommendable process from the viewpoints of environmental friendliness as well as production cost, because it uses a large amount of sulfuric acid, forms a large amount of sulfates as by-products and moreover produces a large amount of sulfate-containing waste water.

A known process devised for reducing the amount of sulfuric acid used in the above-mentioned prior art process comprises thermally decomposing the by-produced sulfates to evolve $SO_3$ and recovering the $SO_3$ as sulfuric acid, see U.S. Pat. No. 5,498,790. However, this process requires complicated equipment for recovering sulfuric acid and requires a heavy investment for construction of the equipment.

SUMMARY AND OBJECTS OF THE INVENTION

The present inventors have made extensive study with the object of providing a process for producing 2-hydroxy-4-methylthiobutanoic acid which permits a reduction of the amount of sulfuric acid used, a reduction of the sulfate-containing waste water produced and a reduction of production cost, and is therefore more environmental-friendly than before. As the result, it has been found that, in the process for producing 2-hydroxy-4-methylthiobutanoic acid by using sulfuric acid, (1) ammonium bisulfate contained in the aqueous layer, which has been discarded in the prior art process, has a capability to hydrate and hydrolyze 2-hydroxy-4-methylthiobutyronitrile, and combined use of ammonium bisulfate and sulfuric acid unexpectedly promotes the hydration and hydrolysis, (2) even when the aqueous layer contains ammonium bisulfate and ammonium sulfate in admixture, addition of a specific substance to the aqueous layer makes it possible to separate the two ammonium salts efficiently from each other and to recover ammonium bisulfate selectively, and (3) re-use of a part or all of the ammonium bisulfate-containing solution obtained after separating ammonium sulfate from the aqueous layer in the above-mentioned hydration and/or hydrolysis of 2-hydroxy-4-methylthiobutyronitrile provides a process for producing 2-hydroxy-4-methylthiobutanoic acid which permits the reduction of the amount of sulfuric acid used, the remarkable reduction of the amount of sulfate-containing waste water and the reduction of the production cost, and is therefore environmental-friendly. The present invention has been accomplished on the basis of the above findings.

Thus, the present invention provides a method for separating ammonium sulfate and ammonium bisulfate from each other which comprises adding a water-miscible organic solvent to an aqueous solution containing ammonium sulfate and ammonium bisulfate to deposit the ammonium sulfate and separating the ammonium sulfate from the aqueous solution.

The present invention further provides a method for producing 2-hydroxy-4-methylthiobutanoic acid which comprises conducting hydration and successive hydrolysis of 2-hydroxy-4-methylthiobutyronitrile in a reaction system containing 2-hydroxy-4-methylthiobutyronitrile and sulfuric acid, ammonium bisulfate being added to the reaction system while conducting the hydration and/or the hydrolysis.

The present invention still further provides a process for producing 2-hydroxy-4-methylthiobutanoic acid which includes the above two methods. Specifically, the process includes:

a process for producing 2-hydroxy-4-methylthiobutanoic acid which comprises the steps of:
(A) conducting hydration and successive hydrolysis of 2-hydroxy-4-methylthiobutyronitrile in a reaction system containing 2-hydroxy-4-methylthiobutyronitrile and sulfuric acid, ammonium bisulfate being added to the reaction system while conducting the hydration and/or the hydrolysis, to obtain a solution containing 2-hydroxy-4-methylthiobutanoic acid,
(B) separating the solution containing 2-hydroxy-4-methylthiobutanoic acid into an organic layer containing 2-hydroxy-4-methylthiobutanoic acid and an aqueous layer containing ammonium sulfate and ammonium bisulfate,
(C) obtaining 2-hydroxy-4-methylthiobutanoic acid from the organic layer, and
(D) adding a water-miscible organic solvent to the aqueous layer to deposit the ammonium sulfate and separating the ammonium sulfate from the aqueous layer; and
more specifically, a process for producing 2-hydroxy-4-methylthiobutanoic acid which comprises the steps of:
(A) conducting hydration and successive hydrolysis of 2-hydroxy-4-methylthiobutyronitrile in a reaction system containing 2-hydroxy-4-methylthiobutyronitrile and sulfuric acid, ammonium bisulfate being added to the reaction system while conducting the hydration and/or the hydrolysis, to obtain a solution containing 2-hydroxy-4-methylthiobutanoic acid,
(B) separating the solution containing 2-hydroxy-4-methylthiobutanoic acid into an organic layer containing 2-hydroxy-4-methylthiobutanoic acid and an aqueous layer containing ammonium sulfate and ammonium bisulfate,
(C) obtaining 2-hydroxy-4-methylthiobutanoic acid from the organic layer,
(D1) adding a water-miscible organic solvent to the aqueous layer to deposit the ammonium sulfate and separating and recovering the ammonium sulfate from the aqueous layer, to obtain a solution containing ammonium bisulfate and the water-miscible organic solvent,
(D2) removing the water-miscible organic solvent from the solution containing ammonium bisulfate and the water-miscible organic solvent, to obtain a solution containing ammonium bisulfate, and (D3) returning a part or all of the solution containing ammonium bisulfate to the step (A).

DETAILED DESCRIPTION OF THE INVENTION

Figure 1:
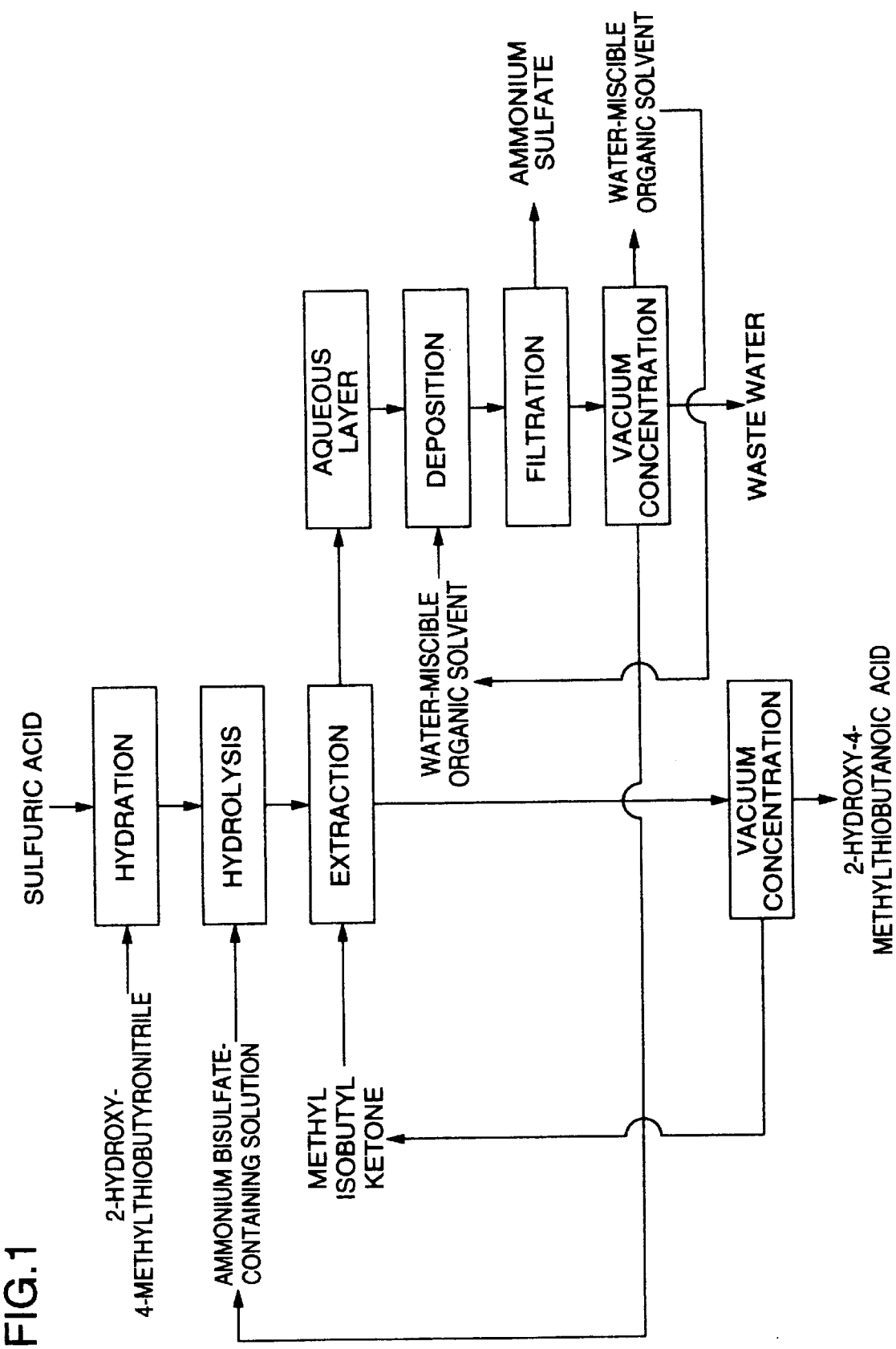
FIG. 1 is a flow sheet showing one embodiment of the present invention as a block diagram wherein a solvent extraction method is used.

In the present invention, in hydrating and hydrolyzing 2-hydroxy-4-methylthiobutyronitrile by using sulfuric acid, ammonium bisulfate is used together with the sulfuric acid at the time of the hydration and/or the hydrolysis to obtain 2-hydroxy-4-methylthiobutanoic acid. A part or all of the ammonium bisulfate used herein can be that by-produced in the above-mentioned series of reaction system. In the present invention, therefore, the part or all of ammonium bisulfate by-produced in the above-mentioned reaction system can be returned to the reaction system and can be used in combination with sulfuric acid for the hydration and/or the hydrolysis in the reaction system.

2-Hydroxy-4-methylthiobutyronitrile forms 2-hydroxy-4-methylthiobutanamide by hydration, which then forms 2-hydroxy-4-methylthiobutanoic acid by hydrolysis. In the present invention, ammonium bisulfate can be used either in the hydration or in the hydrolysis or in the both reactions. When ammonium bisulfate is used in the hydration and succeedingly the hydrolysis is initiated while the bisulfate is allowed to remain in the reaction system, the ammonium bisulfate added at the time of hydration contributes again to the hydrolysis since ammonium bisulfate is substantially kept unconsumed in the hydration, and hence there is no need to add ammonium bisulfate anew at the time of hydrolysis. Combined use of ammonium bisulfate and sulfuric acid in either the hydration or the hydrolysis or both permits a reduction of the required amount of sulfuric acid to be used as well as acceleration of overall reaction rate as compared with the use of sulfuric acid alone.

The manner to carry out the process according to the present invention which comprises hydrating and hydrolyzing 2-hydroxy-4-methylthiobutyronitrile is not particularly limited so long as ammonium bisulfate is used in combination with sulfuric acid in either or both of the reactions. A preferred method of practicing the process is to add 2-hydroxy-4-methylthiobutyronitrile to sulfuric acid or a solution containing sulfuric acid to initiate the reactions. In the present invention, the amount of sulfuric acid used preferably falls within the approximate range of from 0.5 to 1 mole per mole of 2-hydroxy-4-methylthiobutyronitrile.

When ammonium bisulfate is used at the time of hydration, it is preferable that the ammonium bisulfate is made to be present beforehand in a solution containing sulfuric acid, and thereafter 2-hydroxy-4-methylthiobutyronitrile is added thereto. The concentration of sulfuric acid in the solution before the addition of 2-hydroxy-4-methylthiobutyronitrile thereto preferably falls within the approximate range of from 60 to 75% by weight based on the solution without ammonium bisulfate. When the concentration of sulfuric acid in the solution after the addition of 2-hydroxy-4-methylthiobutyronitrile thereto does not fall within the range, it is preferably adjusted by adding additional sulfuric acid so as to fall within the range, i.e., 60 to 75% by weight based on the solution without both organic substances and ammonium bisulfate. The reaction temperature of hydration is preferably about 70° C. or below, more preferably about 40–60° C. The amount of ammonium bisulfate used in the hydration is not particularly restricted. It is preferably such an amount as not to cause the deposition of sulfates after the hydrolysis reaction. The molar amount of ammonium bisulfate may suitably be, as a guide, 1–3 times, preferably about 2 times the molar amount which is calculated by subtracting that of sulfuric acid (used in combination with ammonium bisulfate) from that of 2-hydroxy-4-methylthiobutyronitrile used. The reaction time of hydration varies depending on the each amount of sulfuric acid and ammonium bisulfate used. For example, in the case where the concentration of sulfuric acid in the solution after the addition of 2-hydroxy-4-methylthiobutyronitrile is about 60–75% by weight based on the solution without both organic substances and ammonium bisulfate, and about 0.5–1 mole of sulfuric acid and about 0.1–0.5 mole of ammonium bisulfate are used respectively per 1 mole of 2-hydroxy-4-methylthiobutyronitrile used, the reaction is allowed to continue for about 3 hours at the longest, usually for about 1–2 hours.

In the hydrolysis, the concentration of sulfuric acid in the reaction mixture is preferably adjusted to 25–40% by weight based on the reaction mixture without both organic substances and ammonium bisulfate. In the case where ammonium bisulfate is added at the time of hydrolysis, a convenient method for adjusting the concentration is to prepare an aqueous solution of ammonium bisulfate as the source of the bisulfate and add the solution to a reaction mixture so that the concentration of sulfuric acid in the reaction mixture may fall in the range specified above. The amount of ammonium bisulfate is not particularly limited. It is preferably such an amount that may not cause deposition of sulfates after the hydrolysis reaction. The suitable molar amount of ammonium bisulfate to be used can be, as a guide, 1–3 times, preferably about 2 times the molar amount which is calculated by subtracting that of sulfuric acid (used in combination with ammonium bisulfate) from that of 2-hydroxy-4-methylthiobutyronitrile used. The higher the reaction temperature, the more repidly the reaction proceeds. Considering that the boiling point of the reaction system is about 115° C. at atmospheric pressure, the reaction is preferably conducted substantially in the neighborhood of that temperature. However, if the reaction is conducted at a higher temperature under applied pressure, the reaction proceeds more rapidly. The reaction time of hydrolysis varies depending on the each amount of sulfuric acid and ammonium bisulfate used. For example, in the case where the concentration of sulfuric acid in the reaction mixture is about 35–40% by weight based on the reaction mixture without both organic substances and ammonium bisulfate and where about 0.5–1 mole of sulfuric acid and about 0.2–1 mole of ammonium bisulfate are used respectively per 1 mole of the starting material used, i.e., 2-hydroxy-4-methylthiobutyronitrile used, the reaction is allowed to continue for about 5 hours at the most, usually for about 2–4 hours. After completion of the hydrolysis, the reaction mixture can be further kept in the neighborhood of reaction temperature while stirring for several ten minutes to 1 hour (this operation being hereinafter referred to as the aging treatment).

After the hydrolysis, the reaction mixture obtained is separated into an aqueous layer and an oil layer of 2-hydroxy-4-methylthiobutanoic acid, so that the reaction product can be subjected, as it is, to a layer separation to isolate the objective product, 2-hydroxy-4-methylthiobutanoic acid. Alternatively, 2-hydroxy-4-methylthiobutanoic acid can be extracted from the reaction mixture by using a water-immiscible solvent. The latter method of a solvent extraction can be regarded as a more desirable method, because the aqueous layer left behind the solvent extraction substantially contains only ammonium bisulfate and ammonium sulfate. The water-immiscible solvents suitably used include various ketones and carboxylic acid alkyl esters. Specific examples thereof include methyl isobutyl ketone, methyl n-propyl ketone, methyl ethyl ketone, ethyl butyl ketone, isobutyl ketone, ethyl acetate, n-butyl acetate, n-propyl acetate and isopropyl acetate.

The reaction mixture after the completion of the reactions contains a large amount of ammonium salts. To prevent the deposition of the ammonium salts, the reaction mixture is preferably kept at a temperature of 30° C. or above during the operation of the above-mentioned layer separation or solvent extraction. By conducting the above-mentioned layer separation or solvent extraction, an oil layer containing 2-hydroxy-4-methylthiobutanoic acid and an aqueous layer containing ammonium sulfate and ammonium bisulfate can be obtained from the reaction mixture after the hydrolysis.

The above-mentioned aqueous layer obtained by separating 2-hydroxy-4-methylthiobutanoic acid from the reaction mixture after the hydrolysis is then subjected to a depositing operation by adding a water-miscible organic solvent thereto. By this operation, ammonium sulfate alone is deposited almost selectively from the aqueous layer. Consequently, the resulting mixture can be separated by a separating operation, for example, such a simple operation as filtration, into white crystalline ammonium sulfate and a solution containing ammonium bisulfate. When a part of the ammonium salts has happened to deposit in the reaction mixture before the depositing operation, it is preferable to add first a suitable amount of water and then a water-miscible organic solvent to the reaction mixture before initiating the deposition.

The depositing operation is conducted preferably at room temperature or below, specifically at about 30° C. or below, more preferably at about 20° C. or below. The depositing operation at a high temperature exceeding about 30° C. is undesirable, because there is a potential risk of contamination of ammonium sulfate in the liquid layer.

Water-miscible organic solvents used for the deposition include, for example, lower alcohols, e.g., methanol, ethanol, propanol, isopropanol and butanol, acetone and acetonitrile. The amount of the water-miscible organic solvent used for the deposition varies depending on the concentrations and the molar ratio of ammonium sulfate and ammonium bisulfate in the aqueous layer. For example, in the case where the deposition is applied to an aqueous layer containing 5–30% by weight of ammonium sulfate and 5–40% by weight of ammonium bisulfate at room temperature, the water-miscible organic solvent is added to the aqueous layer in an amount of preferably about 0.2–2 times, more preferably about 0.4–1.5 times that of the aqueous layer in weight basis. When the concentration of the ammonium salts in the aqueous layer is not definitely known or the concentration is outside the above-mentioned range, the water-miscible organic solvent can be added to the aqueous layer until white crystals cease to form in the layer.

By conducting the separating operation subsequent to the depositing operation, white crystalline ammonium sulfate and a solution containing ammonium bisulfate are obtained. The ammonium sulfate obtained can be, if necessary and desired, subjected to a purifying operation, such as washing, to obtain a product with higher purity. The solution containing ammonium bisulfate is, after removal of the water-miscible organic solvent by a vacuum evaporation etc., returned to the step of hydration and/or hydrolysis of 2-hydroxy-4-methylthiobutyronitrile and used in combination with sulfuric acid.

Thus, according to the present invention, substantially the whole amount of ammonium bisulfate formed as a by-product in the production of 2-hydroxy-4-methylthiobutanoic acid can be returned to and used in the course of the production process, specifically the step of hydration and/or hydrolysis of 2-hydroxy-4-methylthiobutyronitrile, whereby a process for producing 2-hydroxy-4-methylthiobutanoic acid substantially without producing waste water can be constituted.

In the foregoing, the method for separating ammonium sulfate and ammonium bisulfate from each other according to the present invention was described with an example wherein the method was applied to the process for producing 2-hydroxy-4-methylthiobutanoic acid. However, the method for separating ammonium sulfate and ammonium bisulfate from each other according to the present invention can be applied not only to the process for producing 2-hydroxy-4-methylthiobutanoic acid but also to other processes in which sulfuric acid is used, for example, to the hydrolysis of acetone cyanhydrin, acrylonitrile, methacrylonitrile and the like; that is, the method can be similarly applied to an aqueous solution in which ammonium sulfate and ammonium bisulfate are present in admixture in such production processes. The conditions under which the method for the separation according to the present invention is to be applied are substantially the same as described in the above process for producing 2-hydroxy-4-methylthiobutanoic acid. In principle, no modification is needed depending on the process to which the method is applied. The method for separating ammonium sulfate and ammonium bisulfate from each other according to the present invention can also be applied to cases where ammonium sulfate and ammonium bisulfate are present as a mixture of powdery crystals. Specific methods to be used in such cases include, for example:

a method which comprises adding a mixture containing ammonium sulfate and ammonium bisulfate to a mixed solution of water and a water-miscible organic solvent to dissolve ammonium bisulfate selectively and then subjecting the resulting mixture to a separating operation such as filtration, and a method which comprises first dissolving the mixture in water to form an aqueous solution of the two ammonium salts, then adding a water-miscible organic solvent to the solution to deposit ammonium sulfate selectively, and subjecting the resulting mixture to a separating operation, such as filtration. The former method is more preferably used than the latter method.

Figure 2:
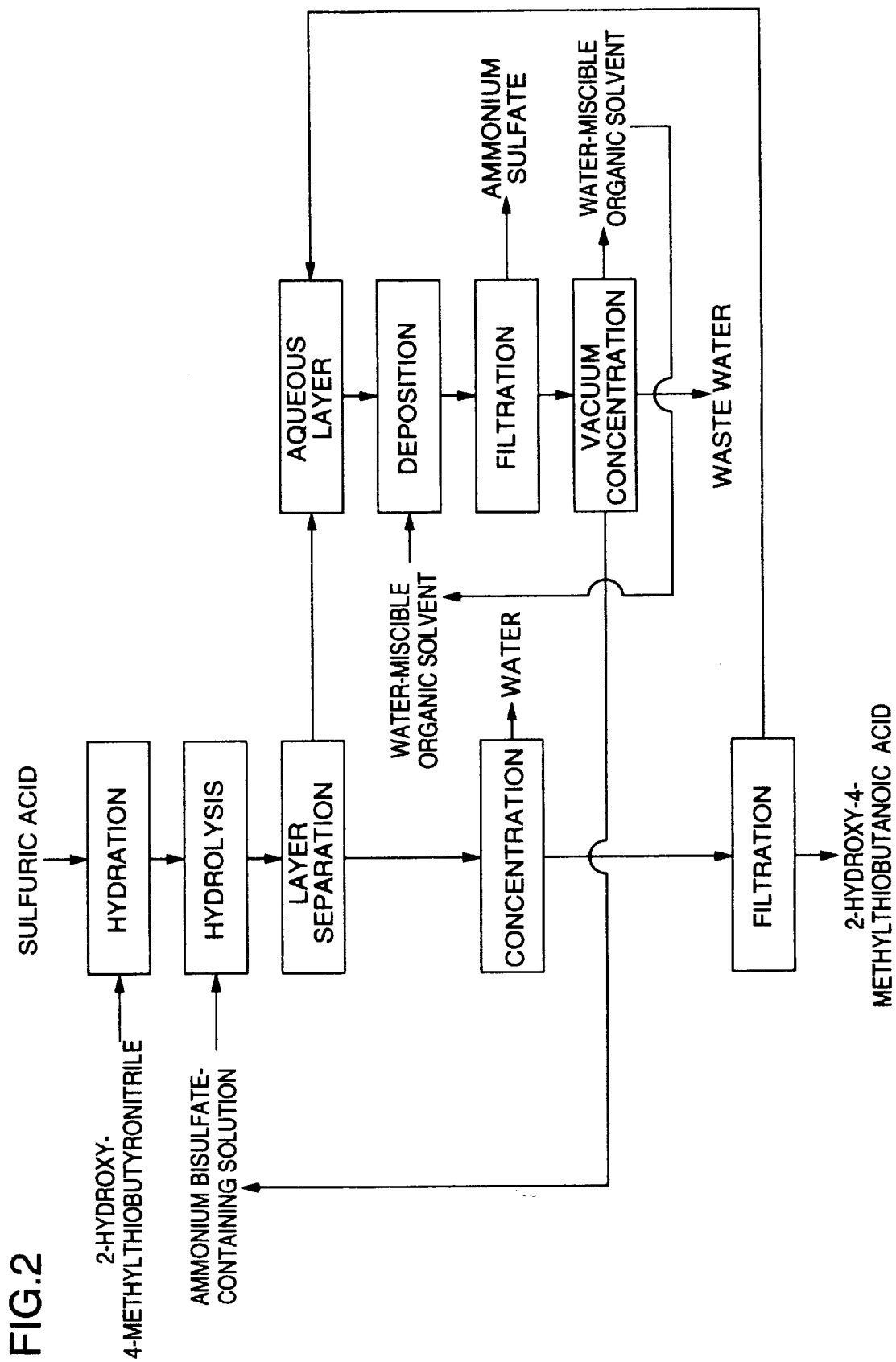
FIG. 2 is a flow sheet showing another embodiment of the present invention as a block diagram wherein a layer separation method is used.

Some embodiments of the present invention are described below with reference to accompanying drawings. FIGS. 1 and 2 are each a flow sheet showing one embodiment of the process for producing 2-hydroxy-4-methylthiobutanoic acid according to the present invention, as a block diagram. In FIG. 1, first a sulfuric acid solution is charged into a reaction vessel while stirring, then 2-hydroxy-4-methylthiobutyronitrile is added thereto, and the resulting mixture is aged for more than ten minutes to several hours while stirring, to cause hydration. To the resulting reaction mixture is then added a solution containing ammonium bisulfate obtained as described later, if necessary together with water, so that the concentration of the sulfuric acid initially charged may become about 25–40% by weight based on the reaction mixture excluding both organic substances and ammonium bisulfate, to cause hydrolysis. After completion of the hydrolysis, the reaction mixture may be kept at approximately the same temperature as the hydrolysis temperature for about more than ten minutes to several hours while stirring to conduct aging.

Then the reaction mixture after hydrolysis is subjected to the next step of isolating the objective product, 2-hydroxy-4-methylthiobutanoic acid, from the reaction mixture. Specific examples of the method used in the step are the solvent extraction method shown in FIG. 1 and the layer separation method shown in FIG. 2. When the method of the solvent extraction is used, a water-immiscible solvent, such as methyl isobutyl ketone, is added to the reaction mixture to conduct the extraction and the resulting oil layer containing extracted 2-hydroxy-4-methylthiobutanoic acid, the objective product, and the resulting aqueous layer are separated from each other. The 2-hydroxy-4-methylthiobutanoic acid obtained by the extraction may be, according to necessity, purified by completely distilling off the water-immiscible solvent, such as methyl isobutyl ketone, by such operations as concentration under vacuum. The water-immiscible solvent, such as methyl isobutyl ketone, recovered by the distillation can be returned to the step of extracting 2-hydroxy-4-methylthiobutanoic acid. When the method of the layer separation is used, the reaction mixture after hydrolysis is, as such, separated into an oil layer containing 2-hydroxy-4-methylthiobutanoic acid and an aqueous layer. The 2-hydroxy-4-methylthiobutanoic acid may be purified by removing water from the oil layer containing 2-hydroxy-4-methylthiobutanoic acid obtained by the layer separation to concentrate the oil layer, and separating and removing thus deposited ammonium sulfate and ammonium bisulfate by such operation as filtration. In this case, when, in advance to concentrating the oil layer, ammonium bisulfate in the oil layer is converted to ammonium sulfate by adding ammonia to the oil layer, the above-mentioned separation and removal are facilitated. The ammonium sulfate and the ammonium bisulfate thus obtained can be mixed with the aqueous layer obtained by the layer separation after the hydrolysis as mentioned above and subjected, together with the aqueous layer, to a subsequent operation, e.g., a depositing operation by adding a water-miscible solvent.

As described above, a water-miscible organic solvent is added to the aqueous layer obtained after separating 2-hydroxy-4-methylthiobutanoic acid from the hydrolysis reaction mixture by the solvent extraction method or the layer separation method, to deposit ammonium sulfate, which is then separated from the aqueous layer by such an operation as filtration. Then the water-miscible organic solvent is removed and recovered by such an operation as vacuum evaporation from the solution remaining after the separation of ammonium sulfate, to obtain a solution containing ammonium bisulfate.

The ammonium bisulfate-containing solution thus obtained can be returned to the steps of the above-mentioned hydration and/or hydrolysis, and is used, together with sulfuric acid, for the hydration and/or hydrolysis in the steps. Although FIGS. 1 and 2 show examples wherein the recovered ammonium bisulfate-containing solution is returned to and is reused in the step of hydrolysis alone, the solution can also be returned to and be reused in the step of hydration alone or in both of the steps. Although the recovered ammonium bisulfate-containing solution is preferably entirely recycled and reused, it is not always necessary to recycle the whole amount and, if necessary from the operational balance, a part of the solution can be discarded as waste water.

According to the process of the present invention set forth above, in the production of 2-hydroxy-4-methylthiobutanoic acid, ammonium bisulfate formed as a by-product is separated from ammonium sulfate and, without being discarded, is returned to and is reused in the reaction system of the production; resultantly the amount of sulfuric acid used can be reduced and the load of waste water can be greatly decreased. Thus, the invention is of great industrial value not only from the viewpoint of production cost reduction but also in environmental friendliness.

The entire disclosure of Japanese Patent Application No. 9-49029 filed on Mar. 4, 1997 and Japanese Patent Application No. 9-248592 filed Sep. 12, 1997, both including specification, claims, drawings and summary, are incorporated herein by reference in their entirety.

EXAMPLES

The present invention is described in detail below with reference to Examples, but the invention is in no way limited thereto.

The quantitative analyses of organic substances were made by liquid chromatography. The quantitative analyses of ammonium bisulfate and ammonium sulfate were made by neutralization titration with sodium hydroxide.

Example 1

In 54.6 ml of water were dissolved 26.4 g (0.2 mole) of ammonium sulfate and 34.5 g (0.3 mole) of ammonium bisulfate. To the resulting solution (115.5 g) was added methanol at 20° C. in an amount of 30 g (a), 50 g (b), 70 g (C) or 100 g (d). Each of the resulting mixtures was stirred for 1 minute and white crystals thus formed were separated by filtration (samples (a) to (d)). As a Comparative Example, the above-mentioned solution was, without addition of methanol, concentrated by 30% under reduced pressure at 50° C., then cooled to room temperature and the deposit formed was separated by filtration (sample (e)).

The respective deposits and filtrates thus obtained were analyzed for their composition. Table 1 shows the results. It reveals that use of a water-miscible organic solvent according to the method for separation of the present invention enables an effective separation of ammonium sulfate and ammonium bisulfate from each other.

TABLE 1

| Amount of methanol added | | Ammonium sulfate (mole) | Ammonium bisulfate (mole) |
|---|---|---|---|
| a) 30 g | Deposit | 0.1190 | 0.0078 |
| | Filtrate | 0.0785 | 0.2855 |
| b) 50 g | Deposit | 0.1787 | 0.0117 |
| | Filtrate | 0.0206 | 0.2867 |
| c) 70 g | Deposit | 0.1961 | 0.0086 |
| | Filtrate | 0.0029 | 0.2929 |
| d) 100 g | Deposit | 0.1930 | 0.0110 |
| | Filtrate | 0.0027 | 0.2861 |
| e) No Addition (comparative Example) | Deposit | 0.1545 | 0.1857 |
| | Filtrate | 0.0391 | 0.1036 |

Example 2

Mixtures of ammonium bisulfate and ammonium sulfate with compositions shown in Table 2 were each dissolved in 34.5 ml of water. To each of the resulting aqueous solutions (64–65 g) was added 39 g of methanol at 20° C., the resulting mixture was stirred for about 1 minute and then the deposit thus formed was separated by filtration. The respective deposits and filtrates were analyzed for their composition, and the results are shown in Table 2. Table 2 reveals that, according to the method for separation of the present invention which uses a water-miscible organic solvent, ammonium sulfate and ammonium bisulfate can be efficiently separated from each other irrespective of the mixing ratio of ammonium sulfate to ammonium bisulfate.

TABLE 2

| Composition of mixture used | | | | | |
|---|---|---|---|---|---|
| Ammonium bisulfate (mole) | Ammonium sulfate (mole) | Ammonium bisulfate/ ammonium sulfate (molar ratio) | | Ammonium sulfate (mole) | Ammonium bisulfate (mole) |
| 0.2 | 0.05 | 4.0 | Deposit | 0.0483 | 0.0038 |
|  |  |  | Filtrate | 0.0 | 0.2052 |
| 0.15 | 0.1 | 1.5 | Deposit | 0.0920 | 0.0052 |
|  |  |  | Filtrate | 0.0007 | 0.1448 |
| 0.125 | 0.125 | 1.0 | Deposit | 0.1141 | 0.0046 |
|  |  |  | Filtrate | 0.0038 | 0.1141 |
| 0.1 | 0.15 | 0.67 | Deposit | 0.1383 | 0.0039 |
|  |  |  | Filtrate | 0.0052 | 0.0988 |

Example 3

48 Grams of methanol was respectively added to 80 g of an aqueous solution each containing 0.13 mole of ammonium sulfate and 0.165 mole of ammonium bisulfate while keeping the temperature of the solutions respectively at 30° C., 50° C. or 70° C. The resulting mixtures were stirred for about 30 seconds and then were rapidly filtered to separate the deposits formed. The respective deposits and filtrates were analyzed for their composition, and the results are shown in Table 3. Table 3 reveals that, according to the method for separation of the present invention which uses a water-miscible organic solvent, ammonium sulfate and ammonium bisulfate can be efficiently separated from each other irrespective of the temperature of separating treatment.

TABLE 3

| Treatment temperature | | Ammonium sulfate (mole) | Ammonium bisulfate (mole) |
|---|---|---|---|
| 30° C. | Deposit | 0.115 | 0.007 |
|  | Filtrate | 0.013 | 0.159 |
| 50° C. | Deposit | 0.102 | 0.006 |
|  | Filtrate | 0.025 | 0.158 |
| 70° C. | Deposit | 0.094 | 0.005 |
|  | Filtrate | 0.035 | 0.159 |

Example 4

To 50 g each of aqueous solutions each containing 0.07 mole of ammonium sulfate and 0.1 mole of ammonium bisulfate was respectively added 25 g of methanol, 50 g of methanol, 25 g of ethanol or 50 g of ethanol. The resulting mixture were stirred for about 1 minute and were respectively filtered to separate the deposits formed. The respective deposits and filtrates were analyzed for their composition, and the results are shown in Table 4. Table 4 reveals that, according to the method for separation of the present invention which uses a water-miscible organic solvent, ammonium sulfate and ammonium bisulfate can be efficiently separated from each other.

TABLE 4

|  |  | Ammonium sulfate (mole) | Ammonium bisulfate (mole) |
|---|---|---|---|
| Methanol 25 g | Deposit | 0.053 | 0.003 |
|  | Filtrate | 0.016 | 0.096 |
| Methanol 50 g | Deposit | 0.068 | 0.003 |
|  | Filtrate | 0.003 | 0.095 |
| Ethanol 25 g | Deposit | 0.037 | 0.002 |
|  | Filtrate | 0.034 | 0.098 |
| Ethanol 50 g | Deposit | 0.069 | 0.004 |
|  | Filtrate | 0.002 | 0.094 |

Example 5

To a solution (a) consisting essentially of 35.5 g (0.25 mole) of 69 wt. % sulfuric acid and 11 g (0.1 mole) of ammonium bisulfate was added dropwise 65.5 g (0.5 mole) of 2-hydroxy-4-methylthiobutyronitrile over 1 hour, then the resulting solution was kept at 50° C. to cause hydration. The solution was sampled at time intervals to examine the change of the amount of 2-hydroxy-4-methylthiobutyronitrile remaining in the solution with the lapse of time. The results obtained are shown in Table 5. For comparison, an experiment was conducted in the same manner as described above except that a solution (b) consisting essentially of 35.5 g (0.25 mole) of 69 wt. % sulfuric acid was used in place of the solution (a) consisting essentially of 35.5 g (0.25 mole) of 69 wt. % sulfuric acid and 11 g (0.1 mole) of ammonium bisulfate. The results thus obtained are also shown in Table 5. Table 5 reveals that, according to the process of the present invention which uses sulfuric acid and ammonium bisulfate, 2-hydroxy-4-methylthiobutyronitrile is rapidly consumed and the hydration reaction proceeds rapidly.

TABLE 5

Quantitative analysis of 2-hydroxy-4-methylthiobutyronitrile

| Time elapsed after dropwise addition | 0 hr | 0.5 hr | 1 hr | 1.5 hr | 2 hr | 3 hr |
|---|---|---|---|---|---|---|
| Example 5 (solution (a) was used) | 0.0654 mole | 0.0165 mole | 0.0062 mole | 0.0018 mole | 0.0007 mole | 0.0004 mole |
| Comparative Example (solution (b) was used) | 0.0880 mole | 0.0257 mole | 0.0102 mole | 0.0053 mole | 0.0025 mole | 0.0013 mole |

Example 6

To a solution (a) consisting essentially of 94.7 g (0.25 mole) of 30 wt. % sulfuric acid and 28.8 g (0.25 mole) of ammonium bisulfate was added 75.1 g (0.5 mole) of 2-hydroxy-4-methylthiobutanamide to cause hydrolysis. The resulting solution was sampled at time intervals to examine the change of the amount of 2-hydroxy-4-methylthiobutanamide remaining in the solution with the lapse of time. The results thus obtained are shown in Table 6. For comparison an experiment was conducted in the same manner as described above except that a solution (b) consisting essentially of 98 g (0.3 mole) of 30 wt. % sulfuric acid was used in place of the solution (a) consisting essentially of 94.7 g (0.25 mole) of 30 wt. % sulfuric acid and 28.8 g (0.25 mole) of ammonium bisulfate. The results thus obtained are also shown in Table 6. Table 6 reveals that, according to the process of the present invention which uses sulfuric acid and ammonium bisulfate, 2-hydroxy-4-methylthiobutanamide is rapidly consumed and the hydrolysis reaction proceeds rapidly.

TABLE 6

Quantitative analysis of 2-hydroxy-4-methylthiobutanamide

| Time elapsed | 1 hr | 2 hr | 3 hr | 4 hr |
|---|---|---|---|---|
| Example 6 (Solution (a) was used) | 0.0616 mole | 0.0200 mole | 0.0071 mole | 0.0031 mole |
| Comparative Example (Solution (b) was used) | 0.0585 mole | 0.0331 mole | 0.0207 mole | 0.0123 mole |

Example 7

To 90.5 g (0.6 mole) of 65 wt. % sulfuric acid was added dropwise 131.2 g (1.0 mole) of 2-hydroxy-4-methylthiobutyronitrile over 1 hour. During the dropwise addition and over a period of 2 hours after the addition, the temperature of the reaction mixture was adjusted to about 50° C. Thereafter 106 ml of an aqueous solution containing 46 g (0.4 mole) of ammonium bisulfate was added to the reaction mixture to adjust the concentration of sulfuric acid to 30% by weight based on the entire reaction mixture excluding both organic substances and ammonium bisulfate. The reaction mixture was then kept at a reaction temperature of 115° C. under reflux for 4 hours. The reaction mixture, while being kept at the high temperature, was subjected to an extracting operation using 160 g of methyl isobutyl ketone to obtain an oil layer containing 2-hydroxy-4-methylthiobutanoic acid and an aqueous layer. The aqueous layer obtained was subjected again to an extracting operation using 100 g of methyl isobutyl ketone. The oil layer thus obtained was combined with the oil layer obtained before. Methyl isobutyl ketone was distilled off from the combined oil layer to obtain 152 g of a liver brown liquid. It was confirmed by a liquid chromatographic analysis that an almost pure 2-hydroxy-4-methylthiobutanoic acid was obtained. Yield 94.5% (including the yield of dimer thereof). The above results reveal that, according to the process of the present invention which uses sulfuric acid and ammonium bisulfate, 2-hydroxy-4-methylthiobutanoic acid can be obtained in a high yield.

Example 8

To 216 g of the aqueous layer obtained after two times of the extracting operations in Example 7 was added at room temperature 60% by weight, based on the aqueous layer, of methanol (130 g). Then 80 g of the deposit thus formed was removed by filtration to obtain 258 g of a filtrate. Methanol was distilled off from the filtrate under reduced pressure so as to give a total amount of the filtrate of 106 ml. The filtrate and the deposit were analyzed for their composition and the results are shown in Table 7. Table 7 reveals that, according to the method for separation of the present invention which uses a water-miscible organic solvent, ammonium sulfate and ammonium bisulfate can be efficiently separated from each other.

TABLE 7

| | Ammonium bisulfate (mole) | Ammonium sulfate (mole) |
|---|---|---|
| Deposit | 0.0524 | 0.4038 |
| Filtrate | 0.4710 | 0 |

Example 9

(1) To 90.5 g (0.6 mole) of 65 wt. % sulfuric acid was added dropwise 131.2 g (1.0 mole) of 2-hydroxy-4-methylthiobutyronitrile over 1 hour, and the mixture was allowed to react at 5° C. for 2 hours. (2) To the reaction mixture was added about 106 ml of a filtrate obtained in the same manner as in Example 8, and the resulting solution was kept at 115° C. under reflux for 4 hours. (3) Then the solution was subjected to an reacting operation by using 0.4 time by weight of methyl isobutyl ketone based on the solution to obtain an oil layer containing 2-hydroxy-4-methylthiobutanoic acid and an aqueous layer. The aqueous layer obtained was subjected to an extracting operation again by using 0.4 time by weight of methyl isobutyl ketone based on the aqueous layer, and the oil layer thus obtained was combined with the oil layer obtained before. The combined oil layer was washed with 50 ml of water, and then methyl isobutyl ketone was distilled off under reduced pressure from the oil layer to obtain 2-hydroxy-4-methylthiobutanoic acid. On the other hand, (4) the aqueous layer obtained after two times of the extracting operations was subjected to the same operation as in Example 8 to obtain 106 ml of a filtrate containing ammonium bisulfate as the main component and a deposit. (5) Then the procedures of (1) through (4) described above were repeated except that 106 ml of the filtrate obtained above was used in the procedure of (2), that is, the solution containing ammonium bisulfate as the main component was recycled and reused, to obtain 2-hydroxy-4-methylthiobutanoic acid. These procedures were repeated two times (that is, the procedures of (1) through (4) were conducted three times in all). The yield of 2-hydroxy-4-methylthiobutanoic acid obtained each time in the procedure (3) and the compositions of the filtrate and the deposit obtained each time in the procedure (4) are summarized in Table 8. Table 8 reveals that, according to the method for separation of the present invention which uses a water-miscible organic solvent, ammonium sulfate and ammonium bisulfate can be efficiently separated from an aqueous solution containing ammonium sulfate and ammonium bisulfate formed in the production of 2-hydroxy-4-methylthiobutanoic acid, and that the ammonium bisulfate obtained by the above-mentioned separation can be returned to and used in the production of 2-hydroxy-4-methylthiobutanoic acid without lowering the yield of the acid and without lowering the efficiency in separating ammonium sulfate and ammonium bisulfate from each other.

TABLE 8

| | 2-Hydroxy-4-methyl-thiobutanoic acid yield *) | Deposit | | Filtrate | |
| --- | --- | --- | --- | --- | --- |
| | | Ammonium bisulfate (mole) | Ammonium sulfate (mole) | Ammonium bisulfate (mole) | Ammonium sulfate (mole) |
| 1st Time | 92.1% | 0.0570 | 0.4120 | 0.5252 | 0 |
| 2nd Time | 91.7% | 0.0620 | 0.4066 | 0.6118 | 0 |
| 3rd Time | 91.8% | 0.1398 | 0.4138 | 0.6270 | 0 |

Note: *) yield including that of dimer

What is claimed is:

1. A process for producing 2-hydroxy-4-methylthiobutanoic acid which comprises conducting hydration and successive hydrolysis of 2-hydroxy-4-methylthiobutyronitrile in a reaction system containing 2-hydroxy-4-methylthiobutyronitrile and sulfuric acid, ammonium bisulfate being added to the reaction system while conducting the hydration and/or the hydrolysis.

2. A process for producing 2-hydroxy-4-methylthiobutanoic acid which comprises the steps of:

(A) conducting hydration and successive hydrolysis of 2-hydroxy-4-methylthiobutyronitrile in a reaction system containing 2-hydroxy-4-methylthiobutyronitrile and sulfuric acid, ammonium bisulfate being added to the reaction system while conducting the hydration and/or the hydrolysis, to obtain a solution containing 2-hydroxy-4-methylthiobutanoic acid, (B) separating the solution containing 2-hydroxy-4-methylthiobutanoic acid into an organic layer containing 2-hydroxy-4-methylthiobutanoic acid and an aqueous layer containing ammonium sulfate and ammonium bisulfate, (C) obtaining 2-hydroxy-4-methylthiobutanoic acid from the organic layer, and (D) adding a water-miscible organic solvent to the aqueous layer to deposit the ammonium sulfate and separating the ammonium sulfate from the aqueous layer.

3. The process of claim 2, wherein the step (D) includes the steps of:

(D1) adding a water-miscible organic solvent to the aqueous layer to deposit the ammonium sulfate and separating and recovering the ammonium sulfate from the aqueous layer, to obtain a solution containing ammonium bisulfate and the water-miscible organic solvent, (D2) removing the water-miscible organic solvent from the solution containing ammonium bisulfate and the water-miscible organic solvent, to obtain a solution containing ammonium bisulfate, and (D3) returning a part or all of the solution containing ammonium bisulfate to the step (A).

4. The process of claim 2, wherein the water-miscible solvent is at least one member selected from the group consisting of methanol, ethanol, propanol, isopropanol, butanol, acetone and acetonitrile.

5. The process of claim 3, wherein the water-miscible solvent is at least one member selected from the group consisting of methanol, ethanol, propanol, isopropanol, butanol, acetone and acetonitrile.

\* \* \* \* \*